US00PP13883P29

(12) United States Plant Patent
Smith

(10) Patent No.: US PP13,883 P2
(45) Date of Patent: Jun. 17, 2003

(54) CHRYSANTHEMUM PLANT NAMED 'YOMARY-JAYNE'

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 10/094,267

(22) Filed: Mar. 8, 2002

(51) Int. Cl.[7] ..... A01H 5/00
(52) U.S. Cl. ..... Plt./294

(58) Field of Search ..... Plt./294

*Primary Examiner*—Bruce R. Campell
*Assistant Examiner*—Annette H. Para
(74) *Attorney, Agent, or Firm*—C. A. Whealy

(57) ABSTRACT

A distinct cultivar of Chrysanthemum plant named 'Yomary-Jayne', characterized by its upright and mounded plant habit; freely branching habit; uniform and freely flowering; anemone-type inflorescences; light pink-colored ray florets and enlarged purple-tipped disc florets; and natural season flowering in early October in the Northern Hemisphere.

1 Drawing Sheet

BOTANICAL CLASSIFICATION/CULTIVAR DESIGNATION

*Chrysanthemum×morifolium* cultivar Yomary-Jayne.

BACKGROUND OF THE INVENTION

The present invention relates to a new and distinct cultivar of Chrysanthemum plant, botanically known as *Chrysanthemum×morifolium,* commercially known as a garden-type Chrysanthemum and hereinafter referred to by the name 'Yomary-Jayne'.

The new cultivar is a product of a planned breeding program conducted by the Inventor in Salinas, Calif. and Fort Myers, Fla. The objective of the breeding program is to create new garden-type Chrysanthemum cultivars having inflorescences with desirable inflorescence forms, attractive floret colors and good garden performance.

The new Chrysanthemum originated from a cross made in January, 1996, in Salinas, Calif., of the Chrysanthemum cultivar Dark Eyes, disclosed in U.S. Plant Pat. No. 8,244, as the female, or seed, parent with the Chrysanthemum cultivar Emily, disclosed in U.S. Plant Pat. No. 7,754, as the male, or pollen, parent. The new Chrysanthemum was discovered and selected by the Inventor as a single flowering plant within the progeny of the stated cross grown in a controlled environment in Fort Myers, Fla. in October, 1998. The selection of this plant was based on its desirable inflorescence form, attractive ray floret color and good garden performance.

Asexual reproduction of the new cultivar by terminal cuttings taken in a controlled environment in Fort Myers, Fla. since December, 1998, has shown that the unique features of this new Chrysanthemum are stable and reproduced true to type in successive generations.

SUMMARY OF THE INVENTION

The cultivar Yomary-Jayne has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yomary-Jayne'. These characteristics in combination distinguish 'Yomary-Jayne' as a new and distinct cultivar:

1. Upright and mounded plant habit.
2. Freely branching habit; dense and full plants.
3. Uniform and freely flowering.
4. Anemone-type inflorescences.
5. Light pink-colored ray florets and enlarged purple-tipped disc florets.
6. Natural season flowering in early October in the Northern Hemisphere.

In side-by-side comparisons conducted in Fort Myers, Fla., plants of the new Chrysanthemum differed from plants of the female parent, the cultivar Dark Eyes, in the following characteristics:

1. Plants of the new Chrysanthemum had a more mounded plant habit than plants of the cultivar Dark Eyes.
2. Plants of the new Chrysanthemum flowered about four to seven days earlier than plants of the cultivar Dark Eyes when flowered under artificial daylength conditions.

In side-by-side comparisons conducted in Fort Myers, Fla., plants of the new Chrysanthemum differed from plants of the male parent, the cultivar Emily, in the following characteristics:

1. Plants of the new Chrysanthemum were shorter than plants of the cultivar Emily.
2. Plants of the new Chrysanthemum flowered about two weeks later than plants of the cultivar Emily when flowered under natural season daylength conditions.
3. Inflorescences of the new Chrysanthemum were anemone types whereas inflorescences of the cultivar Emily were decorative types.

Plants of the new Chrysanthemum can be compared to plants of the cultivar Felicia, disclosed in U.S. Plant Pat. No. 9,809. In side-by-side comparisons conducted in Fort Myers, Fla., plants of the new Chrysanthemum differed from plants of the cultivar Felicia in the following characteristics:

1. Plants of the new Chrysanthemum had a more mounded plant habit than plants of the cultivar Felicia.

2. Plants of the new Chrysanthemum flowered more uniformly than plants of the cultivar Felicia.

3. Plants of the new Chrysanthemum flowered two to three weeks later than plants of the cultivar Felicia when flowered under natural season daylength conditions.

4. Inflorescences of the new Chrysanthemum were anemone types whereas inflorescences of the cultivar Felicia were daisy types.

BRIEF DESCRIPTION OF THE PHOTOGRAPHS

The accompanying photographs illustrate the overall appearance of the new Chrysanthemum. These photographs show the colors as true as it is reasonably possible to obtain in colored reproductions of this type. Colors in the photographs may differ slightly from the color values cited in the detailed botanical description which accurately describe the colors of the new Chrysanthemum.

The photograph at the top of the sheet comprises a side perspective view of a typical flowering plant of 'Yomary-Jayne'.

The photograph at the bottom of the sheet comprises a close-up view of typical inflorescences of the cultivar 'Yomary-Jayne'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in an outdoor nursery in Pendleton, S.C. under natural season conditions and practices which approximate those generally used in commercial garden-type Chrysanthemum production. One rooted cutting was planted in a 16.5-cm container in late July, 2002. Plants were not pinched, that is, the terminal apex was not removed to enhance branching. During the production of the plants, day temperatures ranged from 29 to 32° C. and night temperatures ranged from 16 to 21° C. Measurements and numerical values represent averages for typical flowering plants.

Botanical classification: *Chrysanthemum×morifolium* cultivar Yomary-Jayne.

Commercial classification: Anemone-type garden Chrysanthemum.

Parentage:

*Female, or seed, parent.*—*Chrysanthemum×morifolium* cultivar Dark Eyes, disclosed in U.S. Plant Pat. No. 8,244.

*Male, or pollen, parent.*—*Chrysanthemum×morifolium cultivar* Emily, disclosed in U.S. Plant Pat. No. 7,754.

Propagation:

*Type.*—Terminal tip cuttings.

*Time to initiate roots.*—About four days at 21° C.

*Time to produce a rooted cutting.*—About ten days at 21 ° C.

*Root description.*—White, fine and fibrous.

*Rooting habit.*—Freely branching.

Plant description:

*Appearance.*—Perennial herbaceous anemone-type garden Chrysanthemum. Inverted triangle. Stems initially upright, then somewhat outwardly spreading giving a uniformly mounded appearance to the plant. Freely branching with lateral branches forming at every node.

*Plant height.*—About 23.5 cm.

*Plant diameter.*—About 38 cm.

*Lateral branches.*—Length: About 19 cm. Diameter: About 5 mm. Internode length: About 1.9 cm. Aspect: Upright and outwardly spreading. Texture: Pubescent. Color: 146A.

*Foliage description.*—Leaf arrangement: Alternate. Length: About 5.5 cm. Width: About 4.5 cm. Apex: Cuspidate to mucronate. Base: Mostly truncate. Margin: Palmately lobed, sinuses mostly divergent. Texture: Both surfaces, pubescent; veins prominent on lower surface. Color: Young and mature foliage upper surface: 147A. Young and mature foliage lower surface: 147B. Venation, upper surface: 147A to 147B. Venation, lower surface: 147B. Petiole length: About 1.6 cm. Petiole diameter: About 3 mm. Petiole color: Upper surface: 146A. Lower surface: 146B.

Inflorescence description:

*Appearance.*—Anemone-type inflorescence form with elongated oblong-shaped ray florets and enlarged disc florets. Inflorescences borne on terminals above foliage, arising from leaf axils. Disk and ray florets arranged acropetally on a capitulum. About 4 to 5 inflorescences per lateral.

*Flowering response.*—Under natural season conditions, plants flower in early October in the Northern Hemisphere and continue to flower for at least three weeks depending on weather conditions.

*Inflorescence bud (before showing color).*—Height: About 4.5 mm. Diameter: About 6.5 mm. Phyllary color: Close to 143A.

*Inflorescence size.*—Diameter: About 5.5 cm. Depth (height): About 1.5 cm. Disc diameter: About 3.2 cm, large. Receptacle diameter: About 5.5 mm.

*Ray florets.*—Shape: Elongated oblong. Length: About 2.5 cm. Corolla tube length: About 3 mm. Width: About 8 mm. Apex: Acute, emarginate or dentate. Margin: Entire. Texture: Smooth, glabrous, satiny. Surface: Concave to eventually mostly flat. Orientation: Initially upright, then perpendicular to the peduncle. Number of ray florets per inflorescence: About 41 in about two rows. Color: When opening and fully opened inflorescence, upper surface: White, close to 155D, faintly overlain with 77A; becoming more white with subsequent development. When opening and fully opened inflorescence, lower surface: White, close to 155D, faintly underlain with 77A.

*Disc florets.*—Shape: Enlarged tubular; apex dentate. Length: About 1.2 cm. Width: Apex: About 4 mm. Base: About 1 mm. Number of disc florets per inflorescence: About 265. Color: Immature: Apex: More red purple than 77A. Mid-section: Close to 155D. Base: Close to 150D. Mature: Apex: 77A. Mid-section: White, close to 155D, overlain with 77A. Base: 145C.

*Peduncle.*—Aspect: Flexible, angled about 50° from the stem. Length: First peduncle: About 7 cm. Fourth peduncle: About 9.3 cm. Diameter: About 2 mm. Texture: Pubescent. Color: 146A.

*Reproductive organs.*—Androecium: Present on disc florets only. Anther color: 9A. Pollen: Scarce. Pollen color: 12A. Gynoecium: Present on both ray and disc florets.

*Seed.*—Seed production has not been observed.

Disease/pest resistance: Plants of the new Chrysanthemum have not been shown to be resistant to pathogens and pests common to Chrysanthemums.

Garden performance: Plants of the new Chrysanthemum have been observed to be tolerant to rain, wind and temperatures ranging from 0 to more than 40° C.

It is claimed:

1. A new and distinct cultivar of Chrysanthemum plant named 'Yomary-Jayne', as illustrated and described.

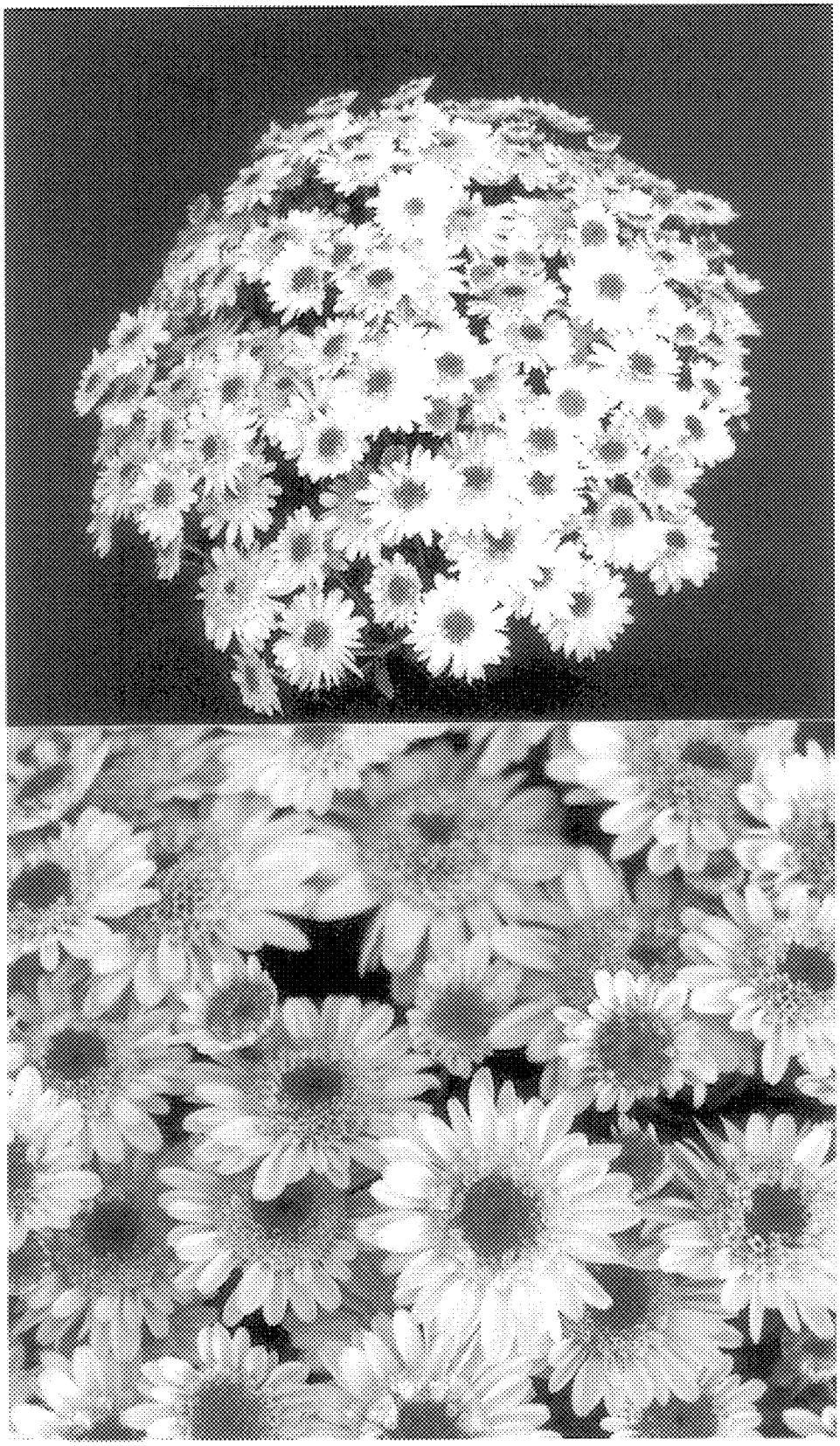

* * * * *